(12) United States Patent
Nietfeld

(10) Patent No.: US 9,607,127 B2
(45) Date of Patent: Mar. 28, 2017

(54) METHODS FOR PROVIDING A SET OF SYMBOLS UNIQUELY DISTINGUISHING AN ORGANISM SUCH AS A HUMAN INDIVIDUAL

(76) Inventor: Jan Jaap Nietfeld, Maarssen (NL)

( * ) Notice: Subject to any disclaimer, the term of this patent is extended or adjusted under 35 U.S.C. 154(b) by 864 days.

(21) Appl. No.: 13/259,439

(22) PCT Filed: Mar. 23, 2010

(86) PCT No.: PCT/EP2010/053793
§ 371 (c)(1),
(2), (4) Date: Mar. 8, 2012

(87) PCT Pub. No.: WO2010/108929
PCT Pub. Date: Sep. 30, 2010

(65) Prior Publication Data
US 2012/0153018 A1   Jun. 21, 2012

Related U.S. Application Data

(60) Provisional application No. 61/210,800, filed on Mar. 23, 2009.

(30) Foreign Application Priority Data

Jul. 30, 2009  (NL) ...................... 2003311

(51) Int. Cl.
*G06F 17/00* (2006.01)
*G06F 19/28* (2011.01)

(52) U.S. Cl.
CPC .................... *G06F 19/28* (2013.01)

(58) Field of Classification Search
USPC ................. 235/375, 379, 380, 492
See application file for complete search history.

(56) References Cited

U.S. PATENT DOCUMENTS

2002/0129251 A1* 9/2002 Itakura et al. ............... 713/176
2003/0182246 A1* 9/2003 Johnson et al. ............... 705/76
2010/0299531 A1* 11/2010 Webster ................. G06Q 50/22
                                                                                     713/189

FOREIGN PATENT DOCUMENTS

EP  1 313 225   5/2003
EP  1 443 449   8/2004
(Continued)

OTHER PUBLICATIONS

Sato et al., "DNA Data Compression in the Post Genome Era", Genome Informatics 2001, 12: pp. 512-514, XP-002571065.
(Continued)

*Primary Examiner* — Michael G Lee
*Assistant Examiner* — Tabitha Chedekel
(74) *Attorney, Agent, or Firm* — Wood, Phillips, Katz, Clark & Mortimer

(57) ABSTRACT

The present invention relates to methods for providing a set of symbols uniquely distinguishing an organism. Specifically, the present invention relates to such method comprising a) providing, in a predetermined order, a number of parameters of said biological characteristic of said sample and their corresponding established values, wherein the combination of said values is uniquely distinguishing said sample; b) translating each corresponding established value of said number of parameters into a single character unique for that individual, established, corresponding value of a particular parameter of said biological characteristic; c) converting said single character into a computer readable code; d) combining said computer readable codes of said single characters into a single string; e) dividing said single string into a set of consecutive segments of a predetermined length; and f) transforming said set of consecutive segments into a set of symbols uniquely distinguishing said biological sample; wherein said predetermined order of said number of (Continued)

parameters of said biological characteristic, and the corresponding established values of step (a) is maintained.

11 Claims, 1 Drawing Sheet

(56) References Cited

FOREIGN PATENT DOCUMENTS

| GB | 2 401 822 | | 11/2004 | |
|----|-----------|---|---------|---|
| KR | 2001-0000472 A | * | 1/2001 | ............... C12Q 3/00 |
| WO | WO 2004/070029 | | 8/2004 | |

OTHER PUBLICATIONS

Giancarlo et al., "Textual Data Compression in Computational Biology: a Synopsis", vol. 25 No. 13 2009, pp. 1575-1586, XP-002571066.

* cited by examiner

METHODS FOR PROVIDING A SET OF SYMBOLS UNIQUELY DISTINGUISHING AN ORGANISM SUCH AS A HUMAN INDIVIDUAL

TECHNICAL FIELD

The present invention relates to methods for providing a set of symbols uniquely distinguishing an organism. Said set of symbols represents a unique biological characteristic, consisting of a set of parameters, of a biological sample, such as nucleic acids or other cellular components, of said organism. Further, the present invention relates to methods for deriving a unique distinguishing biological characteristic from a sample of biological material and using that characteristic to produce a uniform, simple and reduced set of symbols as a biological PIN code, in such a way that when from different samples of biological material the same biological characteristic is derived, the translation and transformation of each characteristic results in an identical set of said symbols forming an identical biological PIN code.

BACKGROUND OF THE INVENTION

Nucleic acid fragments with certain nucleotide sequences have been used for identification purposes. This methodology can be applied to all biological material containing nucleic acids with sequences sufficiently distinguishing the source of the material from a genetically distinct source.

In the past, the fragments were made visible with autoradiography or chemoluminiscence on a chromatographic gel and determining whether a fragment pattern was identical or not to another pattern required visual comparison.

Presently, the detection of nucleic acid fragments is generally performed by using a set of markers for a number of particular sequences in nucleic acids (called "loci") and by using several dyes simultaneously. This produces a pattern of colored bands, which can be converted into a pattern of peaks using an optical read-out system.

The markers are so designed that they only detect a limited number of specific nucleotide sequences or so called "alleles" in the loci. On the basis of so called "ladders" an allele-number can be attributed to the detected nucleotide sequences, or its size can be determined.

Depending on the set of markers used for the determination of a pattern of nucleotide sequences from nucleic acid fragments tables summarizing the determined data can be constructed.

For such tables, the data produced by automated equipment for the detection of nucleotide patterns from nucleic acid fragments derived from a sample of biological material are translated into so called "allele numbers", depicting the number of times a certain allele is repeated in the detected nucleic acid fragment, the so called Short Tandem Repeats or STR's. Such a table, in which the allele numbers are noted in pairs (one for each parent the allele is inherited from), is called a DNA profile, or genetic fingerprint.

Considering the number of possible alleles to be detected per marker, simple mathematics make clear that the more markers are used the less likely a certain pattern of alleles that is found in the nucleic acids in biological material of a specific source will also be found in the nucleic acids in biological material from a genetically distinct source.

For forensic purposes, various marker sets are used, either containing 10 markers, plus the marker AMEL for gender, in the SGM-Plus set, or 13+1 markers in the CODIS set used by the FBI. Even more discriminatory power can be obtained when the 15+1 marker sets called PowerPlex 16 or Identifiler are used.

More recently, methods were published for forensic identification of individuals which are based on panels of SNPs (Single Nucleotide Polymorphisms).

Besides nucleic acid based systems for determining a unique distinguishing biological characteristic of an individual or an organism, other systems have been described to determine other characteristics with such qualities, which are based on other biochemical parameters, like the concentration values of a set specific antibodies or HLA markers.

In forensics, a general format for storing and exchanging DNA profiles is XML. The size of an XML file with the information of such a profile is about 3,000 to 4,000 bytes.

Large databanks with DNA profiles have been set up all over the world, for forensic and other purposes. They have been filled with millions of such profiles and that number is rising quickly. Therefore, the burden on digital systems for the storage, the search and comparison as well as the sending and receiving of a multitude of such data is growing rapidly and might outgrow the capacity of the existing digital systems in the near future. The data files containing SNP-panels are even considerably larger than the forensic XML files.

Another disadvantage of a DNA profile or a SNP panel being depicted as a tables, or an XML file with allele numbers or SNP characters, is that such a multitude of symbols cannot be used to form a single linear barcode or 2 dimensional barcode or matrix code that can be scanned with a hand held scanner.

Yet another disadvantage of DNA profiles using allele numbers of STR's is that the total number of characters is variable since the number of repeats is depicted with 1 to 8 characters per allele.

Considering the above, it is an object, amongst other objects, of the present invention to at least partially, or even completely, solve one or more of the above problems associated with storage and exchange of biological characteristics while maintaining the distinguishing, i.e., characterizing and identifying, capabilities thereof.

SUMMARY OF THE INVENTION

According to the present invention, the above object, amongst other objects, is met by a method as defined in the appended claim 1.

Specifically, the above object, amongst other objects, is met by a method for providing a set of symbols uniquely distinguishing an organism, wherein said set of symbols represents a unique biological characteristic, consisting of a set of parameters, of a biological sample, such as nucleic acids or other cellular components, of said organism, wherein the method comprises:

a) providing, in a predetermined order, a number of parameters of said biological characteristic of said sample and their corresponding established values, wherein the combination of said values is uniquely distinguishing said sample;

b) translating each corresponding established value of said number of parameters into a single character unique for that individual, established, corresponding value of a particular parameter of said biological characteristic;

c) converting said single character into a computer readable code;

d) combining said computer readable codes of said single characters into a single string;
e) dividing said single string into a set of consecutive segments of a predetermined length; and
f) transforming said set of consecutive segments into a set of symbols uniquely distinguishing said biological sample;

wherein said predetermined order of said number of parameters of said biological characteristic, and the corresponding established values of step (a) is maintained during steps (b) to (f), or wherein said order of said parameters is permutated according to a preset protocol.

Because, according to the present invention, the variable number of characters per allele is translated into one single character or symbol, thereby creating a uniform set of characters or symbols per biological characteristic, which after data compression is further transformed into a smaller set of other symbols, which is uniform in size, the methods according to the present invention provide a biological PIN code, or bio-PIN, maintaining the distinguishing, i.e. informative and discriminatory capabilities of the biological characteristic which is derived from said biological sample. Accordingly, the significantly reduced size of a biological PIN code, generally a code being less than 50 bytes, allows that string to be depicted, for example, as a bar code or matrix code that is suitable for a hand held scanner.

The present methods are capable of translating and transforming a distinguishing biological characteristic that is derived from a sample of biological material, for example in the form of a DNA profile, a SNP panel, or another set of biochemical parameters, into a biological PIN code that consists of a set of symbols, which needs up to more than 1000 times less bytes then the original biological characteristic and which is easily sorted/ordered, whereas a list of such codes can be searched very fast.

BRIEF DESCRIPTION OF THE DRAWING

FIG. 1 is a linear bar code representing a bio-PIN.

DETAILED DESCRIPTION

The present methods provide a biological PIN code, or set of symbols uniquely distinguishing an organism by deriving a distinguishing biological characteristic from a sample of biological material and translating and transforming that characteristic into a uniform, simple and reduced set of symbols that forms a biological PIN code. The method functions in such a way that when from different samples of biological material of the same source the same biological characteristic is derived, the translation and transformation of each characteristic results in an identical set of said symbols forming an identical biological PIN code.

The present biological sample is preferably chosen from the group consisting of a body part, organ, tissue, placenta, umbilical cord, blood, body fluid, secreted fluid, cell(s), intracellular organelle(s), intracellular component(s), cell membrane(s), hair(s), extracellular matrix, extracellular component(s), cell product(s), and combinations thereof.

The present biological characteristic is preferably chosen from the group consisting of DNA fingerprinting patterns, Restriction Fragment Length Polymorphism (RFLP) patterns, Polymerase Chain Reaction (PCR) products, Real Time Polymerase Chain Reaction (RTPCR) products, gene expression patterns, protein expression patterns, Single Nucleotide Polymorphisms (SNPs), RNA structures, patterns of RNA levels, genomic mutations, genomic deletions, genomic insertions, genomic organization, cell composition, cell morphology, blood composition, body fluid composition, tissue composition, tissue morphology, extracellular matrix composition, extracellular matrix morphology, protein structures, a pattern of antibody levels, HLA markers, protein levels, lipid structures, lipid levels, carbohydrate structures, carbohydrate levels, proteoglycan structures, proteoglycan levels, glycoprotein structures, glycoprotein levels, glycolipid structures, glycolipid levels, lipoprotein structures, lipoprotein levels, nucleotide structures, nucleotide levels, and combinations thereof.

For the determination of the various biomedical, biological, or biochemical parameters which form said characteristics, the required technologies are known to those skilled in the art.

In a particularly preferred embodiment, the present invention relates to a method comprising the following steps:
1) A biological sample with cells and/or extra-cellular material, containing nucleic acid molecules and/or nucleotides, intra-cellular or extra-cellular, is used for the isolation of cells, or the isolation of extra-cellular nucleic acid molecules and/or nucleotides;
2) The isolation of sub-cellular particles or sub-cellular components from said cells;
3) The isolation of nucleic acid molecules from said sub-cellular particles or components;
4) The fragmentation of said nucleic acid molecules;
5) The determination of specific nucleotide sequences in said fragments, or of specific single nucleotides in said nucleic acid molecules or in said extra-cellular material, which sequences or nucleotides are taken together as the set of parameters which form a unique distinguishing biological characteristic;

Further, the following steps are preferably performed:
6) Arranging the set of parameters which form the distinguishing biological characteristic in a specific predetermined order and in a computer readable form.
7) Computerized simplification of the set of parameters resulting from said determination by translating them into a single character per parameter, producing a uniform set of characters for each sample of biological material;
8) Computerized data compression and dissolving redundancy resulting from said translation, by attribution of one symbol to each unique combination of characters that resulted from said translation, wherein the set of symbols is a computer readable code and either a binary code, or a ternary or quaternary code, or a higher order code than quaternary, wherein the order is limited to maximally the lowest number of said established values among said parameters of said biological characteristic, but preferably a binary code;
9) Computerized concatenation of the symbols resulting from said attribution into a single string; or computerized concatenation of the symbols resulting from said attribution into a single string, plus computerized permutation of the symbols in said string in an order that is determined by generating a set of random numbers with a random number generator running in a computer, wherein there are as many random numbers generated as there are symbols in said string, wherein each symbol is linked to a generated random number and the random numbers are then ranked numerically;
10) Optional computer assisted encryption of said string of concatenated or concatenated and permutated symbols with a fixed key for the encryption of all strings resulting from said concatenation or concatenation and permutation, which enables decryption for those who have the fixed key, or optional computer assisted encryption of said string of concatenated or concatenated and permutated symbols, wherein the encryption is made irreversible, for example by using one way hashing;

11) Computer assisted transformation of the symbols before or after said encryption into other symbols chosen from a set of typographic graphemes, or physics parameters, or a set of other linear, 2-dimensional or 3 dimensional forms, or a set of a higher dimension than 3, which symbols are produced with technologies that make them sensory perceptible and/or machine detectable and which set is large enough to enable to combine 2 or more symbols resulting from said encryption uniquely into 1 symbol that is one of said graphemes, or physics parameters or forms, for further reduction of the eventual number of symbols that is required for the translation and transformation of the parameters of said distinguishing biological characteristic. Preferably the symbols contain a number of bits, created with the code chosen in step 8, that fits N times in the set of other symbols from which the symbols are chosen for the transformation, provided that N is an integer and that extra bits, which are random and without information, are added to the remaining bits in order to reach the number of bits that is required to make the fit;

12) Computer assisted combination of said symbols, which are said graphemes, or physics parameters, or forms into 1 set, producing a single biological PIN code of uniform size.

After biological material has been used to produce a pattern of nucleotide sequences or single nucleotides that is sufficiently distinguishing the source of the material from any other source (with the exception of persons/organisms, which are genetically identical), for the above mentioned particular embodiment of the invention the consecutive steps can be detailed as follows:

1. Register the characteristics of the nucleic acid fragments, including the loci from which the fragments originate and the allele numbers and/or nucleic acid fragment sizes and/or specific nucleotides that were determined.
2. Rank the loci in the nucleic acid to which the fragments or the specific nucleotides belong, according to a preset order.
3. Create a list of symbols for the fragments or the specific nucleotides which can be produced from a specific locus in the nucleic acid, according to a preset order within each group of potential fragments or specific nucleotides belonging to that locus and which order is determined by:
   a) the fragment size and/or
   b) the allele number of the fragments and/or
   c) the specific nucleotide content of the fragments and/or
   d) the specific loci of the fragments in the nucleic acid and/or
   e) any biochemical and/or physics criteria distinguishing the fragments from each other (e.g. the fragment weight or the fragment behaviour in chromatography, or mass spectrometry), which are different from the criteria mentioned under 3.a)-3.d).
4. When so desired, choose the symbols from a set of letters and/or numbers and/or other symbols that will allow the set of symbols to be ordered and/or sorted and/or searched:
   a) numerically and/or
   b) alphabetically and/or
   c) alphanumerically
   d) according to other mathematical or physical characteristics than in a)-c), like frequency of light or sound.
5. Choose the symbols from a set that is large enough to enable to attribute a unique symbol to each of the potential fragments belonging to a specific locus. This means, that the characters in a Latin alphabet would not suffice as a set of single symbols each attributed to one fragment size, or allele number, belonging to a certain locus.
   When using an alphanumerical set of symbols, comprising the digits 1-9 plus the characters in the Latin alphabet, in such a set 35 symbols would be available. Although the digit 0 (zero) could also be included, in a preferable embodiment the 0 (zero) is omitted, to avoid confusion with the character o (the 15$^{th}$ letter of the Latin alphabet).
   Another possibility to create a set of more than 26 symbols is the combination of 2 alphabets, for example the Latin and the Greek alphabet. In that case there would be a set of 50 possible symbols in which the characters can be sorted alphabetically (following the rule that a Greek letter comes after a Latin letter).
   When a set of more than 50 symbols would be required, extra symbols from the ASCII-table could be added. The 3 mentioned possibilities for sets exceeding 26 symbols leave ample room for future expansions of the allele numbers beyond the present maximum of allele numbers per locus.
6. Attribute to each of the fragments produced from said biological material one symbol from a list of symbols prepared for each of the appropriate loci.
7. Combine, per locus, the symbols belonging to that locus in a group.
8. Line up all the groups of ordered symbols according to said ranking of the loci they belong to, thereby forming a code of a single string of symbols, in which each symbol is allocated to a specific place in the line up and represents 1 nucleic acid fragment.
   That concludes the transformation of said sufficiently distinguishing pattern of nucleic acid fragments into a biological PIN code (or bio-PIN).
   Because of the stepwise process of said attribution, ordering and allocation of the symbols in the line-up, it is possible to use only a 1-byte symbol per fragment when forming said biological PIN code.
   Since the code in the example is an alphabetical one (wherein the Greek alphabet comes after the Latin alphabet) and the information is limited to a single string of 32 symbols (or less), which can be stored in 1 data field, digital storing, ordering, sorting, comparing and searching of large numbers of such codes can be performed very fast. The capacity required for storage, sending and receiving such codes is only a fraction of the capacity required for data files containing nucleic acid fragment profiles comprising loci names plus fragment sizes, or allele numbers.
   When a higher degree of data compression has to be achieved, the redundancy in a 1-byte symbol per fragment or per nucleotide can be dissolved by combining symbols into higher order symbols.
   Although a 1-byte symbol requires 8 bits, most alleles can be represented with less than 8 bits. That means that when for example a binary system is used, for most loci the allele numbers can be represented with 5 bits symbols (3 bits being redundant), because these loci count 32 allele numbers or less. When 8 symbols of 5 bits are combined into 5 symbols of 8 bits, a data compression of 37.5% is achieved.
   If 8 bits symbols have to be printable, not all 256 possibilities are available, because not all 256 positions in the ASCII table are printable characters. In that case 5 bits symbols have to be combined into 7 bits or 6 bits symbols.

When different nucleic acid fragment patterns are determined in different systems using different marker sets for different loci, that procedure requires different tables for each of those cases. Then, in order to allow the de-transformation of a certain biological PIN code back to the DNA fingerprint it originated from, one or more additional symbols are added to and included in the bio-PIN. Choosing one or more characters from one of the sets described under point 5, for each of the various tables for the various marker sets, will allow designating a specific table that was used for the transformation. At the recognition of said additional symbol(s) in a bio-PIN, the appropriate table can be used for the de-transformation of that bio-PIN.

There are different possibilities for an encryption step in various embodiments of the present invention.

When it is desirable that the bio-PIN can be de-transformed, back to the underlying unique distinguishing biological characteristic, AES encryption according to the Rijndael standard can be applied (well known to those skilled in the art), while using 1 fixed key for the encryption step during the procedure from each of the unique distinguishing biological characteristics to bio-PINs. In case a list with key numbers would exist, one or more symbols from one of the sets described under point 5 can be added to and included in the biological PIN code, to designate the key that was used for the encryption.

In case it is undesirable that a bio-PIN could be de-transformed, back to the underlying unique distinguishing biological characteristic, an irreversible encryption procedure can be used during the procedure from the unique distinguishing biological characteristic to the bio-PIN. A method for such encryption would be SHA-256, or a comparable one way hashing method, which are well know to those skilled in the art). Another possibility would be to apply said AES encryption, but with a single unique key for each encryption. That can be achieved by a procedure in which the data set which is to be irreversibly encrypted generates its own encryption key according to a fixed recipe that ensures that for an identical data set an identical key is produced and that for each different data set the encryption key is unique.

An embodiment of the present invention in which the biological PIN code cannot be decoded because of an irreversible encryption procedure, would make this embodiment of the present invention particularly suitable for application in forensics. When the biological PIN code cannot be decoded, it means that it cannot be linked back to the underlying unique distinguishing biological characteristic and therefore it cannot be linked to the individual from whom the unique distinguishing biological characteristic was determined. That makes that such a code (which could be named Code-F, where F stands for Forensics) cannot be considered to constitute 'personal data' and therefore it does not fall under the Data Protection Convention.

As a consequence DNA samples and DNA profiles in Forensics, which were designated by the European Court of Human Rights as 'personal data', can be destroyed/deleted once a suspect is not convicted. In stead of the DNA profile in the DNA database, the un-linkable code-F can then be stored in the crime case file.

When at a later point in time the same individual that was previously suspected but not convicted is arrested once more and again a DNA sample is collected and a DNA profile is stored, irrespective of whether the individual is convicted or not, a code-F can be determined again and that code will be identical to the previously determined code-F for that individual. By matching those codes, a suspect in a new crime case can be connected to a previous crime case in which that individual was involved.

It could be undesirable for a particular embodiment of the present invention that the production of a bio-PIN would be copied and applied on a DNA containing sample that possibly would have been collected from an individual without his/her consent. To avoid unauthorized production of a bio-PIN, somewhere in the procedure from the unique distinguishing biological characteristic to the bio-PIN a permutation of the characters/symbols can be performed. If the permutation procedure is kept secret and/or would be securely embedded in a computerized part of the bio-PIN production, then even if the method for determination of the unique distinguishing biological characteristic would become known and also the procedures for the translation, the data compression, encryption and further transformation of the data into a biological PIN code would become know to unauthorized persons, they would not be able to produce the correct bio-PIN as long as they do not know the permutation recipe.

In another preferred embodiment of the invention the method for providing a set of symbols uniquely distinguishing a biological sample wherein said set of symbols represents a unique biological characteristic of said sample, consisting of a set of parameters, comprises the following steps:

a) providing, in a predetermined order, a number of parameters of said biological characteristic of said sample and their corresponding established values, wherein the combination of said values is uniquely distinguishing said sample;

b) translating each corresponding established value of said number of parameters into a single character unique for that individual, established, corresponding value of a particular parameter of said biological characteristic;

c) converting said single character into a computer readable code;

d) combining said computer readable codes of said single characters into a single string;

e) dividing said single string into a set of consecutive segments of a predetermined length; and f) transforming said set of consecutive segments into a set of symbols uniquely distinguishing said biological sample;

wherein said predetermined order of said number of parameters of said biological characteristic, and the corresponding established values of step (a) is maintained during steps (b) to (f), or wherein said order of said parameters is permutated according to a preset protocol. The steps of this last mentioned embodiment can be, according to individual preferred embodiments, detailed as follows:

said computer readable code is a binary code, or a ternary or quaternary code, or a higher order code than quaternary, wherein the order is limited to maximally the lowest number of said established values among said parameters of said biological characteristic, but preferably a binary code.

the number of bits in each of said codes is the minimal number of bits necessary to represent the naturally occurring established corresponding values of said number of parameters of said biological characteristic.

said predetermined length of said segments in said dividing is of a number of bits that fits N times in the set of symbols from which the symbols are chosen when the segments are later transformed into symbols, provided that N is an integer and that extra bits, which are random and without information, are added to the remaining bits in order to form an extra segment, when that is required to make the fit.

said number of parameters of said biological characteristic is chosen from the group consisting of at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31 and 32, or a number ranging from 2 to 104.

said parameters of said biological characteristic are nucleic acid based parameters, each with 2 corresponding established values originating from a diploid genome.

said single character in the translation is chosen from:
a) the ASCII character table, wherein the blanks are filled with characters from the Greek alphabet;
b) the Windows 1252 character table, wherein the blanks are filled with characters from the Greek alphabet;
c) the CP437 character table, wherein the blanks are filled with characters from the Greek alphabet;
d) a collection consisting of a combination of a number of alphabets, wherein the number of different alphabets is large enough to result in a total collection of more than 256 characters;
e) the collection of characters in the Chinese Kangxi Dictionary.

said set of symbols uniquely distinguishing said biological sample in said transformation is sensory perceptible and/or machine detectable and is chosen from:
a) the ASCII character table, wherein the blanks are filled with characters from the Greek alphabet;
b) the Windows 1252 character table, wherein the blanks are filled with characters from the Greek alphabet;
c) the CP437 character table, wherein the blanks are filled with characters from the Greek alphabet;
d) a collection of RGB colors from a collection of colors wherein each of the composing Red, Green and Blue values can vary from 0 to 255, resulting in a collection of maximally 16.777.216 colors;
e) a collection of 2-dimensional arrays, at least larger than the number of characters in the ASCII character table, consisting of a certain number of dots or circles, triangles, squares, polygons, or other goniometric shapes, each shape with a different color, or combinations of such shapes, which occupy various positions in each of the arrays in a way that, depending on the number of dots, or circles, or other goniometric shapes and their possible positions on the array, a collection with a distinct number of arrays is formed which differ from one another;
f) a collection of 3-dimensional bodies, or forms, at least larger than the number of characters in the ASCII character table, consisting of pyramids, cubes or other polyhedral bodies of which some of the vertices are each carrying a different color, in a way that, depending on the number of vertices of a particular type of 3-dimensional bodies, the fraction of their vertices that is color coded and the positions of the color coded vertices on the 3-dimensional bodies, a collection with a distinct number of 3-dimensional bodies is formed which differ from one another;
g) a collection of audio signals which are generated within the limits of a musical instrument or a tone generator;
h) a collection of bar code characters.

said combining further comprises reversible or irreversible encryption of said single string.

use of the set of symbols representing said parameters of said biological characteristic, and their corresponding established values, of a biological sample for uniquely distinguishing a human individual, wherein when said individual is a member of identical twins, or an identical triplet or quadruplet, the birth rank of that individual has been included in said set of symbols.

In yet another preferred embodiment of the invention a procedure is used, comprising the following steps:
1) determination of a unique distinguishing biological characteristic of a biological sample, in the form of a DNA fingerprint.
2) Translation and simplification by converting the allele numbers, representing the values of the parameters of said characteristic, into ASCII characters using a substitution table.
3) Conversion of the ASCII characters into a binary code, using a conversion table, during which for each locus the minimum number of binary bits is applied that is required when attributing a binary code to all allele numbers for that particular locus.
4) String formation in which the binary codes for said characteristic are concatenated into one string of binary bits, or said string formation followed by encryption, which encryption is either reversible, or irreversible.
5) Division of the string of binary bits into segments of 8 bits, which equals 1 byte.
6) Transformation of each segment of 1 byte into an ASCII character, for which purpose the blank spots in the ASCII character table are filled with characters from the Greek alphabet.
7) Combination of the ASCII characters in one set which forms a biological PIN code with uniform size for the underlying biological sample (see FIG. 1 biological PIN code for the result for the example DNA fingerprint, in ASCII characters and in the form of linear barcode).

The present invention will be further detailed in the following example of a preferred embodiment of the present invention.

Example

Table 1 shows on the left hand side an exemplary table of a biological characteristic derived from a biological sample containing nucleic acids. The biological characteristic is defined by 11 parameters, each having 2 values, determined for 2×11 loci in a diploid genome. On the right hand side the table shows the result of the translation of each value of the parameters into a single character unique for that value of the respective parameters. That way the values of the parameters are reduced to a collection of characters which is 22 bits symbols in size.

TABLE 1

| Locus | Allele number | | | | | |
|---|---|---|---|---|---|---|
| AMEL | X | Y | | AMEL | X | Y |
| D3S1358 | 13 | 17 | | D3S1358 | G | T |
| VWA | 12 | 20 | | VWA | C | 2 |
| D16S539 | 8 | 11 | | D16S539 | E | J |
| D2S1338 | 22 | 25 | → | D2S1338 | M | U |
| D8S1179 | 14 | 16 | | D8S1179 | J | N |
| D21S11 | 28 | 31 | | D21S11 | 2 | E |
| D18S51 | 13 | 16 | | D18S51 | 6 | B |
| D19S433 | 12 | 17 | | D19S433 | I | Z |
| TH01 | 6.3 | 9.3 | | TH01 | G | P |
| FGA | 20 | 21 | | FGA | 5 | 9 |

After translation of the values of the parameters into single symbols in table 1, the symbols are converted into a computer readable code, in the present example a binary code, resulting in table 2.

TABLE 2

| X | Y |  | 0 | 1 |
|---|---|---|---|---|
| G | T |  | 00110 | 10001 |
| C | 2 |  | 00010 | 11000 |
| E | J |  | 00100 | 01001 |
| M | U |  | 01100 | 10010 |
| J | N |  | 01001 | 01101 |
| 2 | E |  | 0010001 | 0100100 |
| 6 | B |  | 001100 | 010110 |
| I | Z |  | 01000 | 10111 |
| G | P |  | 00110 | 01110 |
| 5 | 9 |  | 0010100 | 0011000 |

The binary codes are then combined into a single string of bits by placing the codes behind each other working from left to right and top to bottom. That single string reads:
0100110100010001011000001000100101100100100100
1011010010010100100001100010 110010001011100110
0111000101000011000

The above single string can either be first encrypted resulting, for example, in:
10001001010011010110010101100000100100100001
10101100100110100010100000100110011110011000010
111100001010001001 or directly be divided into a set of consecutive segments of a predetermined length, in the present case 8 bits, resulting in 14 segments of 8 bits, or 14 bytes:

```
01001101   00010001   01100000   10001001   01100100   10010010
11010010   00101001   00001100   01011001   00010111   00110011
10001010   00011000
```

A set of symbols uniquely distinguishing an organism is provided by transforming the above segments into a set of symbols. In case the ASCII character table is used for such transformation (filling up the blanks with characters from the Greek alphabet), the above 14 bytes can be transformed into the following biological PIN code:
?=)LNB.1DRC6Hb This bio-PIN can also be represented with the linear bar code shown in FIG. 1.

What is claimed is:

1. A method for deriving a unique distinguishing biological characteristic from a sample of biological material and using that characteristic to produce a reduced set of symbols as a biological PIN code which is uniform in size, while the distinguishing capabilities are maintained, in such a way that when from different samples of biological material the same biological characteristic is derived, the production of said set of symbols results in an identical biological PIN code for each of those samples, comprising the following steps in a suitable order:

a) determination of a unique distinguishing biological characteristic in a sample of biological material, whereas the birth rank is included if the biological material originates from an individual who is a member of identical twins or an identical triplet, or quadruplet;
   b) ordering the parameters of said biological characteristic of said sample of biological material and their corresponding established values according to a predetermined order;
   c) simplification of said characteristic by translation of each of said established values of its parameters into a single character, thereby creating a set of characters per biological characteristic that is uniform in size;
   d) data compression and dissolving the redundancy which is resulting from said translation, leading to a set of symbols that is reduced in the number of symbols, compared to the number of characters in said set of characters;
   e) formation of a single string of symbols by concatenation of the symbols in said set of symbols, or formation of a single string of symbols from said set of symbols and the encryption of said string;
   f) transformation of said string of symbols or said encrypted string of symbols into other symbols, which are sensory perceptible and/or machine detectable;
   g) combination of said other symbols into 1 set, forming a single biological PIN code of uniform size.

2. The method according to claim 1, wherein said sample of biological material is chosen from the group consisting of a body part, organ, placenta, umbilical cord, tissue, body fluid, blood, cell(s), intracellular organelle(s), intracellular component(s), cell membrane(s), extracellular matrix, hair(s), extracellular component(s), secreted fluid, cell product(s) and combinations thereof.

3. The method according to claim 1, wherein said biological characteristic is chosen from the group consisting of tissue composition, tissue morphology, body fluid composition, blood composition, cell composition, cell morphology, genomic organization, genomic mutations, genomic deletions, genomic insertions, gene expression patterns, DNA fingerprinting patterns including Short Tandem Repeat (STR) DNA fragments, Restriction Fragment Length Polymorphism (RFLP) patterns, Polymerase Chain Reaction (PCR) products, Real Time Polymerase Chain Reaction (RTPCR) products, Single Nucleotide Polymorphisms (SNPs), RNA structures, patterns of RNA levels, protein expression patterns, extracellular matrix composition, extracellular matrix morphology, protein structures, protein levels, lipid structures, lipid levels, carbohydrate structures, carbohydrate levels, proteoglycan structures, proteoglycan levels, glycoprotein structures, glycoprotein levels, glycolipid structures, glycolipid levels, lipoprotein structures, lipoprotein levels, nucleotide structures, nucleotide levels, and combinations thereof.

4. The method according to claim 1, wherein the determination of the unique distinguishing biological characteristic from said sample of biological material comprises the following steps:
   a) the isolation of nucleic acid containing cells from said sample that consists of tissue or a body fluid with cells, or the isolation of nucleic acids and/or nucleotides which exist extra-cellular in said samples;
   b) the isolation of sub-cellular particles or sub-cellular components from said cells;
   c) the isolation of nucleic acids and/or nucleotides from said sub-cellular particles or components;
   d) the fragmentation of said nucleic acids;
   e) the determination of specific nucleotide sequences or single nucleotides in said fragments, or said extra-cellular nucleotides, which sequences or nucleotides taken together as a set form a unique distinguishing biological characteristic.

5. Method according to claim 4, wherein the established values of the parameters of said biological characteristic are originating from a diploid genome.

6. The method according to claim 1, wherein the simplification of said characteristic is performed by computerized translation of the established values of the set of parameters resulting from the determination of said characteristic into a single character per parameter.

7. The method according to claim 1, wherein the data compression and dissolving redundancy is performed by computerized attribution of one symbol to each unique combination of characters that resulted from said translation, wherein the set of symbols is of a higher order than the set of characters resulting from the translation.

8. The method according to claim 1, wherein the formation of a single string of symbols is performed by computerized concatenation of said symbols, or by computerized concatenation and random permutation of said symbols, wherein the permutation takes place in an order that is determined by generating a set of random numbers with a random number generator running in a computer, wherein there are as many random numbers generated as there are symbols in said string and wherein each symbol is linked to a generated random number and the random numbers are then ranked numerically.

9. The method according to claim 1, wherein the encryption is computer assisted and uses:

i) an encryption method with a fixed key for all encryptions, enabling decryption by those persons who have that fixed key; or
ii) an encryption method that makes the encryption irreversible.

10. The method according to claim 1, wherein said transformation is computer assisted and said other symbols are chosen from a set of typographic graphemes, or physics parameters, or a set of other linear, 2-dimensional or 3 dimensional forms, or a set of a higher dimension than 3, which set is large enough to enable to combine 2 or more symbols resulting from the steps preceding the transformation uniquely into 1 of the said other symbols that is one of said graphemes, or physics parameters or forms, in order to achieve further reduction of the eventual number of symbols that is required for the translation and transformation of said distinguishing biological characteristic.

11. The method according to claim 1, wherein said combination of other symbols into one biological PIN code is computer assisted.

* * * * *

UNITED STATES PATENT AND TRADEMARK OFFICE
CERTIFICATE OF CORRECTION

PATENT NO. : 9,607,127 B2  
APPLICATION NO. : 13/259439  
DATED : March 28, 2017  
INVENTOR(S) : Jan Jaap Nietfeld Page 1 of 1

It is certified that error appears in the above-identified patent and that said Letters Patent is hereby corrected as shown below:

In the Specification

Column 10, Line 46, "bits" should be deleted from description

Column 11, Lines 18-20,
" 0100110100010001011000001000100101100100100100101101001000101001000011000 10 1100100010111001100111000101000011000"
Should be a continuous binary code
-- 01001101000100010110000010001001011001001001001011010010001010010000110001011001000101110 011001110001010000110000 --

Column 11, Lines 23-25,
" 10001001010011010110010101100000100100100000110101100100110100010100000100 1 100111100110000010111100001010001000 1"
Should be a continuous binary code
-- 1000100101001101011001010110000010010010000011010110010011010001010000010011001111001100 001011110000101000010001 --

Signed and Sealed this  
Sixteenth Day of May, 2017

Michelle K. Lee  
*Director of the United States Patent and Trademark Office*